(12) United States Patent
Yee (10) Patent No.: US 6,416,536 B1
(45) Date of Patent: Jul. 9, 2002

(54) METHOD FOR DEPLOYMENT OF A LOW PROFILE DELIVERY SYSTEM

(75) Inventor: Carl E. Yee, Austin, TX (US)

(73) Assignee: SciMed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/923,898

(22) Filed: Aug. 7, 2001

Related U.S. Application Data (62) Division of application No. 09/337,120, filed on Jun. 21, 1999.

(51) Int. Cl.$^7$ .................................................. A61F 2/06
(52) U.S. Cl. .............................. 623/1.11; 623/1.23
(58) Field of Search ................... 623/1.11, 1.13, 623/1.15, 1.18, 1.19, 1.2, 1.23, 1.44, 1.49; 606/198, 195, 108; 128/898

(56) References Cited

U.S. PATENT DOCUMENTS

| | | | |
|---|---|---|---|
| 4,787,899 A | | 11/1988 | Lazarus |
| 5,122,136 A | | 6/1992 | Guglielmi et al. |
| 5,405,378 A | | 4/1995 | Strecker |
| 5,534,007 A | | 7/1996 | St. Germain et al. |
| 5,683,451 A | | 11/1997 | Lenker et al. |
| 5,693,083 A | * | 12/1997 | Baker et al. ............. 606/195 |
| 5,709,703 A | * | 1/1998 | Lukic et al. ............. 606/198 |
| 5,723,003 A | | 3/1998 | Winston et al. |
| 5,733,267 A | | 3/1998 | Del Toro |
| 5,746,766 A | * | 5/1998 | Edoga ................... 606/191 |
| 5,749,848 A | | 5/1998 | Jang et al. |
| 5,755,777 A | * | 5/1998 | Chuter .................. 606/195 |
| 5,824,041 A | | 10/1998 | Lenker et al. |
| 5,954,764 A | | 9/1999 | Parodi |
| 5,989,280 A | | 11/1999 | Euteneuer et al. |
| 6,136,006 A | | 10/2000 | Johnson et al. |
| 6,139,572 A | | 10/2000 | Campbell et al. |
| 6,146,415 A | | 11/2000 | Fitz |

FOREIGN PATENT DOCUMENTS

| | | | |
|---|---|---|---|
| EP | 0 705 578 | 4/1996 | |
| EP | 0 720 838 | 7/1996 | |
| WO | 93/11823 | 6/1993 | |
| WO | WO 98/09583 | 3/1998 | |
| WO | WO 98/53761 | 12/1998 | |
| WO | WO-0078248 A1 | * 12/2000 | ............. A61F/2/06 |

OTHER PUBLICATIONS

International Search Report dated Sep. 13, 2000.
Written Opinion dated Jul. 11, 2001.

* cited by examiner

Primary Examiner—Corrine McDermott
Assistant Examiner—Hieu Phan
(74) Attorney, Agent, or Firm—Ratner & Prestia (57) ABSTRACT

A delivery system for endoluminal deployment of a stent inside of a biocompatible graft cover minimizes obstruction of endoluminal fluid flow during deployment. The delivery system comprises a stent sheath, a compressed stent underlying the stent sheath, and a graft overlying the stent sheath and releasably retained in a compressed state surrounding the sheath. The graft distal end is attached to the stent at or proximal the stent distal end, and the graft outer surface is exposed to the interior space of the lumen during deployment. The proximal end of the graft may be attached to the stent sheath by a releasable attachment adapted for release during deployment of the stent, or may be otherwise constrained, such as by heat deformation, to remain adjacent the outer circumference of the stent prior to deployment. The releasable attachment may be a suture that is severed by a pusher having a cutter therein. The delivery system may further include an inner core underlying the stent and connected to a tip sheath that overlies the stent distal end. One method of deploying the stent and overlying graft comprises advancing the tip sheath to allow the stent distal end to expand, retracting the stent sheath to cause the suture to be severed by the pusher cutter therefore allowing endoluminal fluid to flow between the graft and the sheath, and then completing deployment of the stent to urge the graft against the lumen wall.

18 Claims, 9 Drawing Sheets

METHOD FOR DEPLOYMENT OF A LOW PROFILE DELIVERY SYSTEM

This application is a divisional of U.S. patent application Ser. No. 09/337,120, filed Jun. 21, 1999 (status: pending).

TECHNICAL FED

The present invention relates generally to endoluminal grafts or "stents" and, more specifically, to a stent delivery system or "introducer" for deploying a stent inside of a prosthetic graft without interrupting fluid flow during deployment and a method for such deployment.

BACKGROUND OF THE INVENTION

A stent is an elongated device used to support an intraluminal wall. In the case of a vascular stenosis, a stent provides an unobstructed conduit for blood in the area of the stenosis. An intraluminal prosthesis may comprise a stent that carries a prosthetic layer of graft material. Such a prosthesis may be used, for example, to treat a vascular aneurysm by removing the pressure on a weakened part of an artery so as to reduce the risk of rupture. Typically, an intraluminal stent or prosthesis is implanted in a blood vessel at the site of a stenosis or aneurysm endoluminally, i.e. by so-called "minimally invasive techniques" in which the stent, restrained in a radially compressed configuration by a sheath or catheter, is delivered by a stent deployment system or "introducer" to the site where it is required. The introducer may enter the body through the patient's skin, or by a "cut down" technique in which the entry blood vessel is exposed by minor surgical means. When the introducer has been threaded into the body lumen to the stent deployment location, the introducer is manipulated to cause the stent to be released from the surrounding sheath or catheter in which it is restrained (or alternatively the surrounding sheath or catheter is retracted from the stent), whereupon the stent expands to a predetermined diameter at the deployment location, and the introducer is withdrawn. Stents are typically expanded by spring elasticity, balloon expansion, or by the self-expansion of a thermally or stress-induced return of a memory material to a pre-conditioned expanded configuration.

Figure 1:
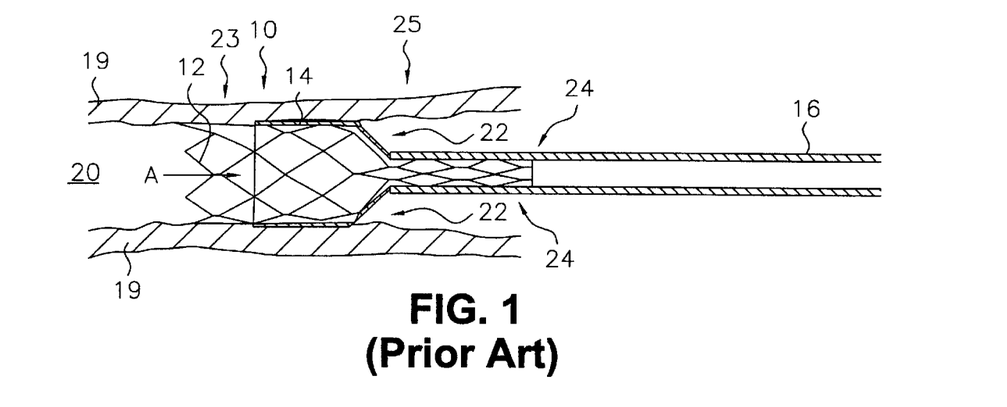
FIG. 1 is a longitudinal section schematic illustration of an exemplary endoluminal prosthesis delivery system of the prior art.

Referring now to a stent deployment system of the prior art in FIG. 1, there is shown an endoluminal prosthesis 10 comprising a wire stent 12 affixed along its length to an outer graft cover 14, the graft and stent compressed inside outer sheath 16 (shown in cross-section). During the deployment process of endoluminal prosthesis 10 in a body lumen 20, such as a blood vessel, outer sheath 16 is retracted, and stent 12 expands against the walls 19 of the lumen 20 (shown in cross-section). During the expansion process, the partially-deployed, covered section 22 at distal end 23 and middle section 25 of integral stent/graft prosthesis 10 can block the flow of blood along arrow A temporarily until proximal end 24 is released from the sheath. As used herein, "proximal" is defined as meaning "closer to the end of the introducer remaining outside the body", whereas "distal" is defined as meaning "farther from the end of the introducer remaining outside the body". During deployment, the pressure of obstructed blood flow at covered section 22 may cause the prosthesis to migrate away from its intended location or become longitudinally compressed. If for some reason the deployment procedure becomes protracted, the blood flow blocked by covered section 22 may impart serious stress upon the patient. Thus, it is desirable to provide for unobstructed blood flow throughout the stent deployment process.

Figure 2:
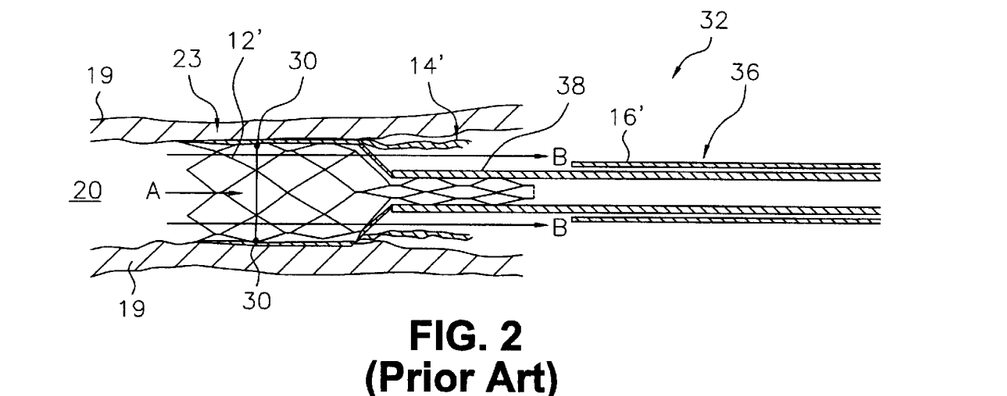
FIG. 2 is a longitudinal section schematic illustration of an exemplary stent delivery system known to the inventor prior to this invention.

A construction known to the inventor prior to this invention comprises a device shown in FIG. 2 comprising stent 12' and outer graft cover 14' joined by a connection 30 to stent 12' proximal the distal end 23 thereof. Prior to deployment, stent 12' and graft liner 14' are restrained in a compressed configuration by an outer sheath 16' surrounding both the stent and the liner, and by an inner sheath 38 disposed between stent 12' and liner 14' proximally of connection 30. Deployment of this prosthesis is effected by first retracting outer sheath 16', allowing distal portion of stent 12' and then cover 14' to fully expand independently. Stent 12' is subsequently fully expanded proximal of the connection point by retracting inner sheath 38. During deployment of this device, blood flow can continue as indicated by arrows B.

The introducer construction having two sheaths as described above necessarily requires an introducer of somewhat larger diameter and lesser flexibility than most such introducers known in the art having only a single sheath.

SUMMARY OF THE INVENTION

The present invention provides a flexible, single-sheath, low-profile delivery system for deployment of a stent inside of a biocompatible graft cover in a distal deployment location in a body lumen from a proximal access location outside the body lumen. The delivery system comprises a stent sheath having a distal end located upstream relative to the fluid flow; a compressed stent underlying the stent sheath, the stent having a proximal end housed within the stent sheath and a distal end; and a compressed biocompatible graft cover overlying the stent sheath along the length of the stent and releasably retained in a compressed state surrounding the sheath. The graft has a distal end attached to the stent at or proximal the stent distal end and an outer surface exposed to the interior space of the lumen during deployment. The stent distal end may be spaced distally from the stent sheath distal end and graft attachment, in which case the delivery system may further comprise a tip sheath overlying the stent distal end and an inner core, optionally having a guidewire lumen therein, attached to the tip and extending axially through the stent. A pusher underlies the stent sheath proximal the stent. The pusher distal end may be rounded. The inner core and attached tip sheath may be attached distally to the pusher, or the pusher may have an inner lumen extending axially therethrough, wherein the inner core extends axially through the pusher inner lumen.

The stent delivery system further may comprise a temporary, protective wrapper over the biocompatible graft, the wrapper adapted to be removed prior to insertion of the delivery system into the body lumen. The compressed biocompatible graft may further comprise a proximal end attached to the stent sheath by a releasable attachment, such as a suture, adapted to be released during deployment of the stent. The suture may be adapted for release by being secured with a slip-knot adapted to be untied during stent deployment, by the delivery system further comprising a balloon adapted for breaking the suture upon inflation of the balloon, or by the pusher further comprising a cutter, such as a sharpened hypotube, adapted for severing the suture upon movement of the pusher relative to the stent sheath.

Specifically, the stent sheath may have a suture connection point, such as a pair of tie-holes, in its circumference and radially-opposite first and second through-holes, with the pusher having a window in its distal end aligned with the stent sheath through-holes and having the cutter proximally located therein. In such a configuration, the opposite ends of the suture are attached to the suture connection point, and an intermediate section of the suture is threaded through the graft in one or more locations, through the sheath through-holes, and through the pusher window.

The invention further comprises a method for endoluminally deploying a stent and overlying biocompatible graft cover without obstructing fluid flow during deployment, as follows. First, the stent and graft are compressed and loaded into a single-sheath-profile stent delivery system as described herein. Then, the stent delivery system is inserted into a body lumen and navigated through the lumen until the stent is at a desired deployment location. Next, the stent sheath is proximally displaced relative to the stent distal end, the stent distal end becomes expanded, and endoluminal fluid flows between the stent sheath and the graft so that the graft becomes radially distanced from the stent sheath. Finally, deployment of the stent is completed so that it biases the graft against the body lumen.

Where the stent delivery system further comprises a tip having a tip sheath overlying the distal end of the stent and attached to an inner core extending axially through the stent, the method further comprises, prior to proximally displacing the stent sheath relative to the stent, first releasing the stent distal end from the tip sheath by displacing the inner core distally relative to the stent sheath. Where the pusher is attached to the inner core, displacing the inner core distally relative to the stent sheath comprises a single, continuous, proximal retraction of the stent sheath that also displaces the pusher distally relative to the stent sheath to deploy the stent. Where the pusher has an inner lumen axially therethrough through which the inner core is mounted, displacing the inner core distally relative to the stent sheath comprises first advancing the inner core distally relative to the stent sheath to release the stent distal end from the tip sheath, and then retracting the stent sheath to deploy the stent. Where the proximal end of the graft is attached to the sheath with a releasable attachment such as a suture, the attachment is released prior to endoluminal fluid flowing between the graft and the sheath. Where the releasable attachment is a suture, the step of moving the stent sheath relative to the pusher may cut the suture.

The method may further comprise suturing the graft to the stent sheath by the steps of anchoring a first end of the suture through the tie-holes, extending the suture along the stent sheath; piercing the graft one or more times with the suture; extending the suture along the stent sheath; entering the stent sheath radially through one of the through-holes, extending the suture through the pusher window, and exiting the stent sheath through the opposite through-hole; extending the suture along the stent sheath; piercing the graft one or more times with the suture; extending the suture semi-circumferentially around the sheath; and anchoring a second end of the suture to the tie-holes.

After deployment, the stent delivery system may be prepared for withdrawal by advancing the pusher into the tip sheath and advancing the stent sheath until the distal end of the stent sheath is adjacent the proximal end of the tip sheath, and then withdrawn. Prior to insertion into the body, the stent sheath may be locked to the pusher and the inner core biased under slight tension and locked to the pusher. In such case, deployment further comprises unlocking the inner core from the pusher prior to moving the inner core distally and unlocking the stent sheath from the pusher prior to retracting the stent sheath.

It is to be understood that both the foregoing general description and the following detailed description are exemplary, but are not restrictive, of the invention.

BRIEF DESCRIPTION OF DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

Figure 3A:
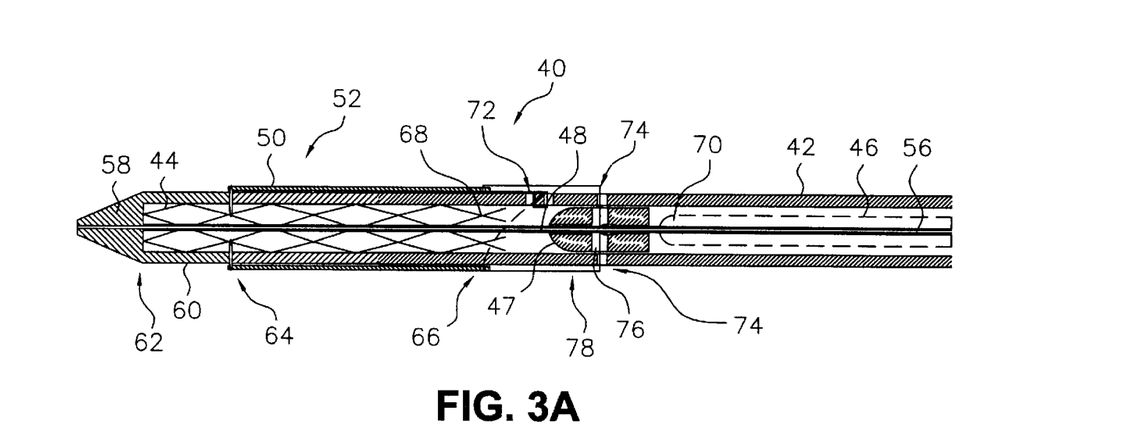
FIGS. 3A–3C are longitudinal section schematic illustrations of an assembled exemplary stent delivery system of the present invention, and enlarged portions thereof, respectively.
Figure 3B:
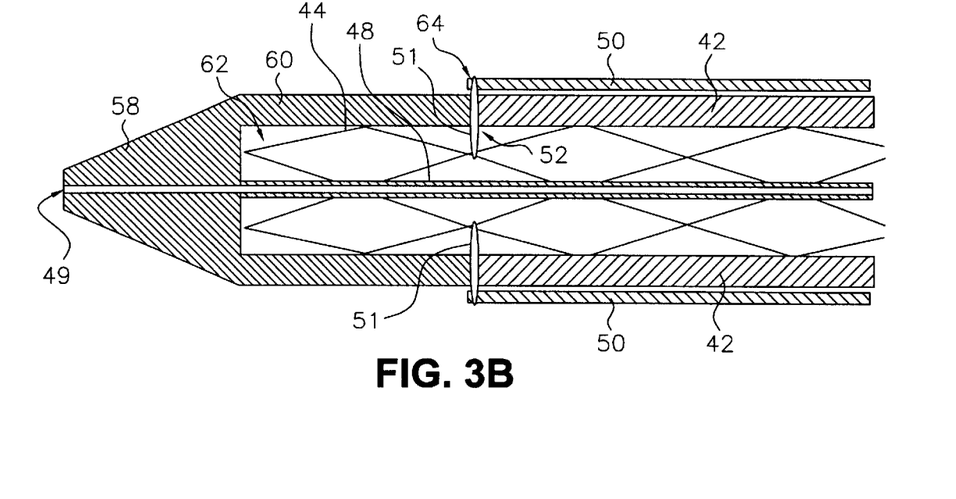
Figure 3C:
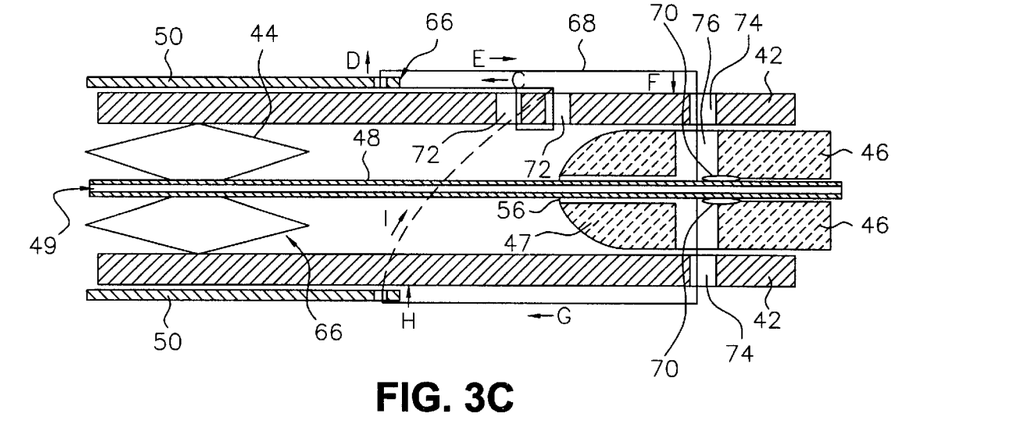

Referring now to the drawing, wherein like reference numerals refer to like elements throughout, FIGS. 3A–3C illustrate an exemplary introducer according to the present invention for endoluminal deployment of a stent inside of a biocompatible graft cover without obstructing endoluminal fluid flow during deployment. As shown in FIGS. 3A–C, exemplary stent delivery system 40 comprises a stent sheath 42, a compressed stent 44 underlying the stent sheath, a pusher 46 underlying the stent sheath proximal to the stent, an inner core 48, and a compressed biocompatible graft 50 overlying distal end 52 of the stent sheath. Inner core 48 is axially mounted within inner lumen 56 of pusher 46, extends axially through stent 44 and attaches to tip 58 comprising tip sheath 60 overlying distal end 62 of the stent. Optional central guidewire lumen 49 (not shown in FIG. 3A) runs through inner core 48 and tip 58, as shown in FIGS. 3B and 3C. Graft 50 has a distal end 64 attached to the stent by attachment 51 distally of the sheath distal end 52. Optionally, attachment 51 may be located at or somewhat proximally of the distal end 52 of sheath 42 within sheath 42, so long as the part of graft 50 lying within sheath 42 is easily pulled or otherwise disposed distally of sheath 42 during deployment. Graft 50 further has a proximal end 66 attached to stent sheath 42 by a releasable attachment, such as suture 68, adapted to be released during deployment of the stent. As shown in FIGS. 3A–C, pusher 46 has a rounded distal end 47.

Although stent delivery system 40 has both a tip sheath 60 and a stent sheath 42, the two sheaths abut one another axially and have the same outer diameter. Thus, the two sheaths together in series form a single-sheath-profile stent delivery system, meaning that the profile of the stent delivery system is no greater than that provided by a single outer sheath plus graft material. Other embodiments having no tip sheath 60, are discussed below.

The stent may be self-expanding, comprising, for example, a shape-memory material such as nitinol, or may be any type of elastically or thermally expandable stent known in the art. The biocompatible graft material may be polyester, polyurethane, polyethylene, polytetrafluoroethylene (PTFE), or any material known in the art. The stent deployment system of the present invention may be used for deployment of stents and grafts within blood vessels or in other body lumens, such as in the trachea. As used herein, the term "stent delivery system" s ball encompass both a completed assembly which is capable of deploying a stent or a sub-assembly which is capable of deploying a stent when combined with other components To effect release of the suture 68 during deployment, pusher 46 filter comprises at distal end 47 a window 76 in which is proximally mounted cutter 70, such as a sharpened hypotube, adapted for severing the suture upon movement of the pusher relative to stent sheath 42. Stent sheath 42 has a connection point, such as a pair of tie-holes 72, as shown in FIG. 3C, and a pair of radially opposite through-holes 74. Window 76 is radially aligned with stent sheath through-holes 74 prior to and during introduction of stent delivery system 40 into the body. As shown in FIG. 3C, suture 68 is anchored at one end through tie-holes 72 and extends distally along stent sheath 42 from the tie-holes along arrow "C", pierces graft 50 one or more times along arrow "D", returns proximally along the stent sheath along arrow "E", turns radially in the direction of arrow "F" and enters the stent sheath through one through-hole 74, extends through pusher window 76 and exits the stent sheath through the other through-hole 74, extends distally along the stent sheath along arrow "G", pierces the graft one or more times along arrow "H", extends semi-circumferentially around the stent sheath along arrow "I" (shown in dashed lines) and anchors to the tie holes or to the other end of the suture. Suture 68 may be attached by a method that follows the order described above, starting along arrow C in alphabetical order through arrow I, or in reverse order, starting in the direction opposite arrow I, and following reverse alphabetical order in the opposite direction of each arrow named above. This suture configuration reduces friction between the suture and graft during deployment because the suture is cut into two short lengths to be pulled through the graft rather than one long length of suture.

Other suture configurations may also be used to anchor graft 50 to stent sheath 42 and to cut the suture upon deployment. Instead of the suture being tied through a pair of tie holes 72, the suture connection point to stent sheath 42 may comprise any type of connection known in the ant. Such connection may comprise, for example without limitation thereto, a single hole in the stent sheath and a stopper knot tied in the end of the suture to prevent pulling the end through the hole, an adhesive or heat-fused bond, or a crimped metal or rubber band.

Figure 4A:
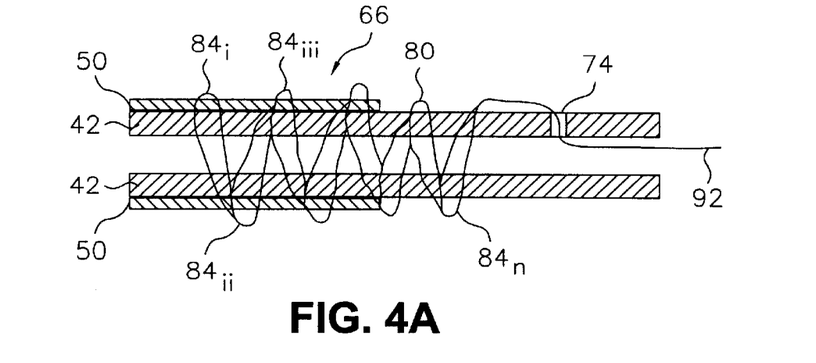
FIGS. 4A and 4B are schematic illustrations of a crochet weave securing a graft to the stent sheath, shown in partial longitudinal section, and of the loops of an exemplary crochet configuration, respectively.
Figure 4B:
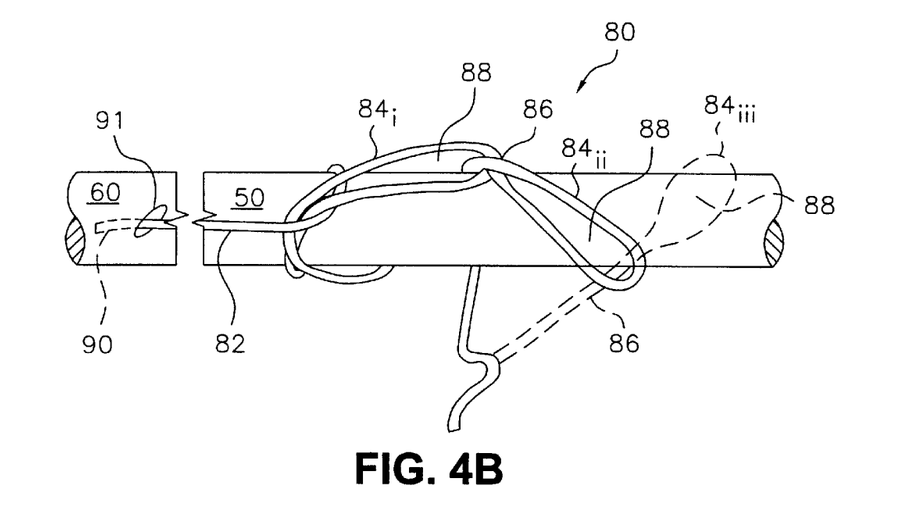

Different releasable attachment devices other than sutures may also be used. In an alternative embodiment, referring now to FIGS. 4A and 4B, a crochet weave 80 may be disposed over proximal end 66 of graft 50 to secure it to stent sheath 42. As shown in detail in FIG. 4B, crochet weave 80 comprises a continuous filament 82 wound into n successive loops 84*i–n* helically wrapped around the graft in alternating orientations (loop 84*i* counterclockwise, loop 84*ii* clockwise, loop 84*iii* counterclockwise, and so on, viewed from loop 84*i* looking proximally), the stem 86 of each loop protruding through the hole 88 made by the preceding loop. Distal end 90 of filament 82 is typically releasably secured to provide resistance to unwinding of crochet weave 80, such as by being pulled through a slot 91 in tip sheath 60 and pinched therein. Proximal end 92 of the filament is tucked within through-hole 74 in stent sheath 42, as shown in FIG. 4A, and trailed within the stent sheath to the outside of the body. Filament 82 may then be pulled like a drawstring to untie crochet weave 80 loop by loop and to pull distal end 90 out of slot 91. Although FIG. 4A shows sheath 42 and graft 50 in longitudinal section to illustrate through-hole 74 and trailing proximal end 92, crochet weave 80 is illustrated in its entirety without hidden portions, to show location. FIG. 4B shows crochet weave 80 as visible from one side of graft 50.

Figure 5:
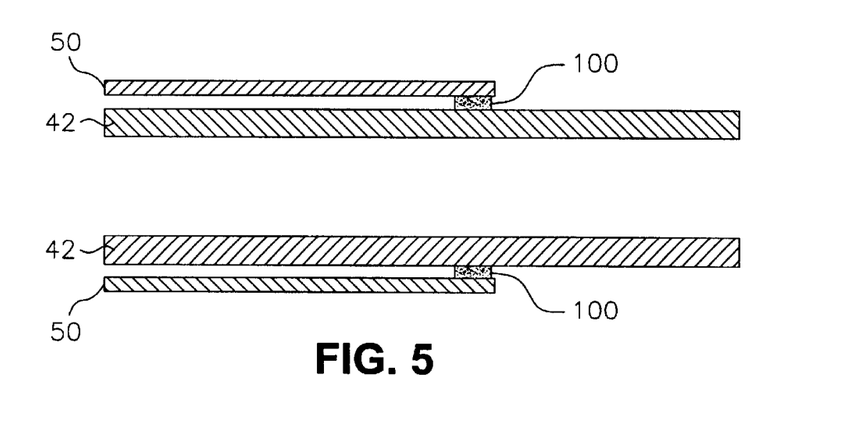
FIG. 5 is a longitudinal section schematic illustration of a graft secured to the stent sheath with an adhesive.

In another alternative embodiment, referring now to FIG. 5, graft 50 may be tacked to stent sheath 42 with a bead of biocompatible adhesive 100 that softens or dissolves after a certain amount of time of exposure to blood (or other intraluminal fluid in the lumen in which the stent is to be deployed), thus allowing the graft to be pulled away from stent sheath 42 upon deployment.

Figure 6A:
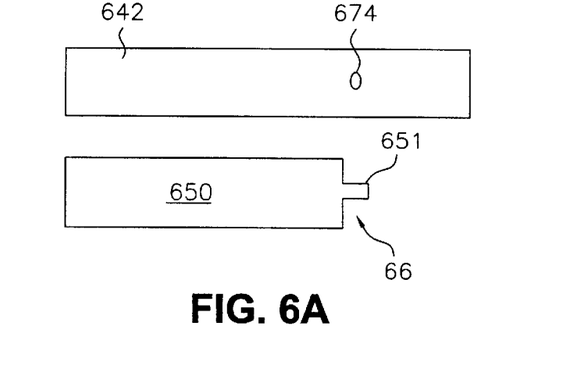
FIGS. 6A–6C are schematic illustrations of an exemplary graft and an exemplary stent sheath to which the graft is adapted to be releasably secured, a longitudinal section of such graft and stent sheath showing the graft in a secured configuration, and a longitudinal section of the graft and stent sheath showing the graft in a released configuration.
Figure 6B:
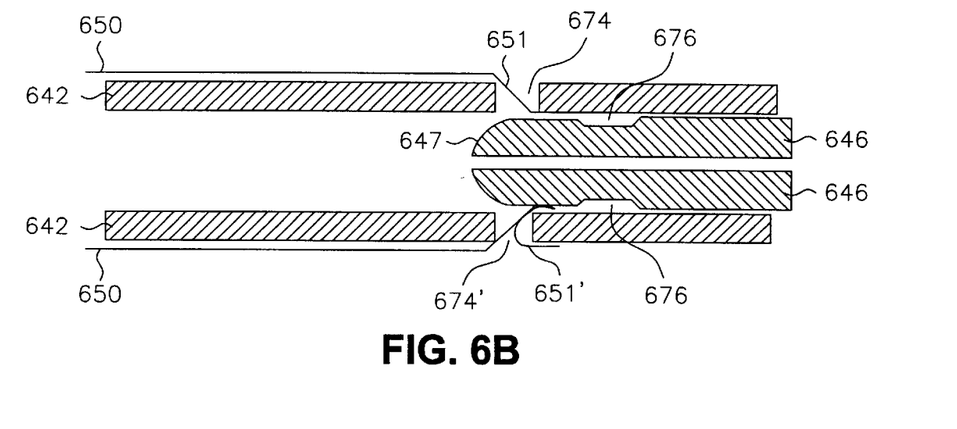
Figure 6C:
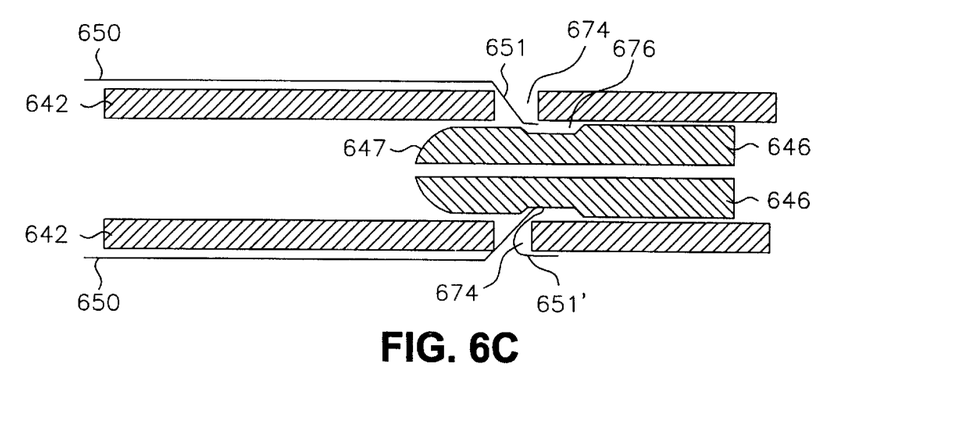

In yet another alternative embodiment, referring now to FIGS. 6A–6C, graft 650 may have a tab 651 at the proximal end 66 thereof, the tab adapted to be inserted in slot 674 in stent sheath 642. Tab 651 is then releasably secured by being pinched between stent sheath 642 and pusher 646, as shown in FIG. 6B. Pusher 646 has an indent 676 adjacent the pusher distal end 647 such that when sheath 642 is retracted proximally or pusher 646 is advanced distally, indent 676 aligns with slot 674 in stent sheath 642 such that tab 651 is released and graft 650 is free to deploy, as shown in FIG. 6C. As shown in FIGS. 6B and 6C, tab 651 may be completely inserted within slot 674 and its end pinched between pusher 676 and the inside wall of stent sheath 642 as shown with respect to top slot 674, or as shown with respect to bottom through-hole 674', portion 651' of graft 650 may be doubled over on itself with the end outside the slot. Portion 651' inserted within slot 674' may be a discrete tab, or if the materials of construction of graft 650 so allow, portion 651' may rather be a portion of graft 650 that is merely pushed into through-hole 674, doubled over on itself, and pinched.

Figure 7A:
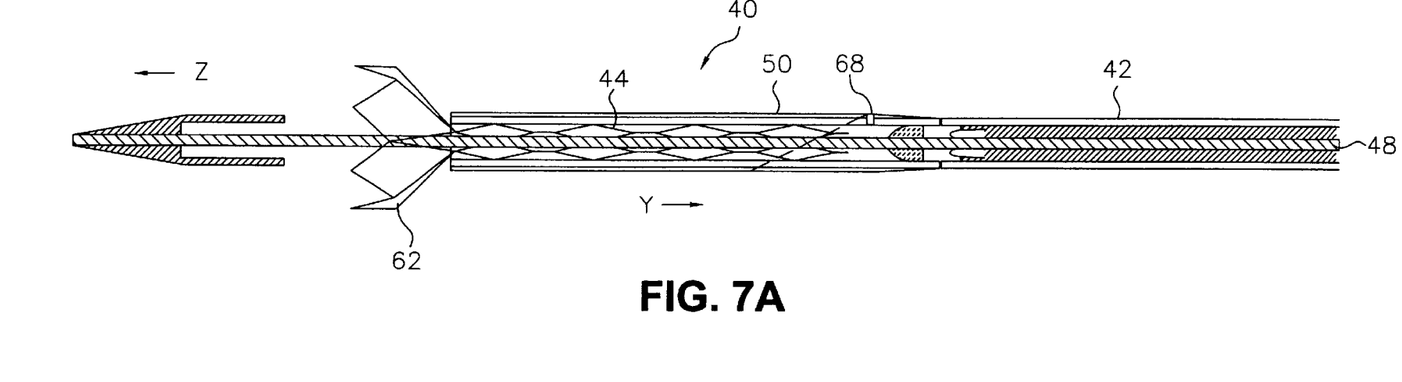
FIGS. 7A–7C are longitudinal section schematic illustrations of the stent delivery system of FIGS. 3A–3C during sequential deployment steps.
Figure 7B:
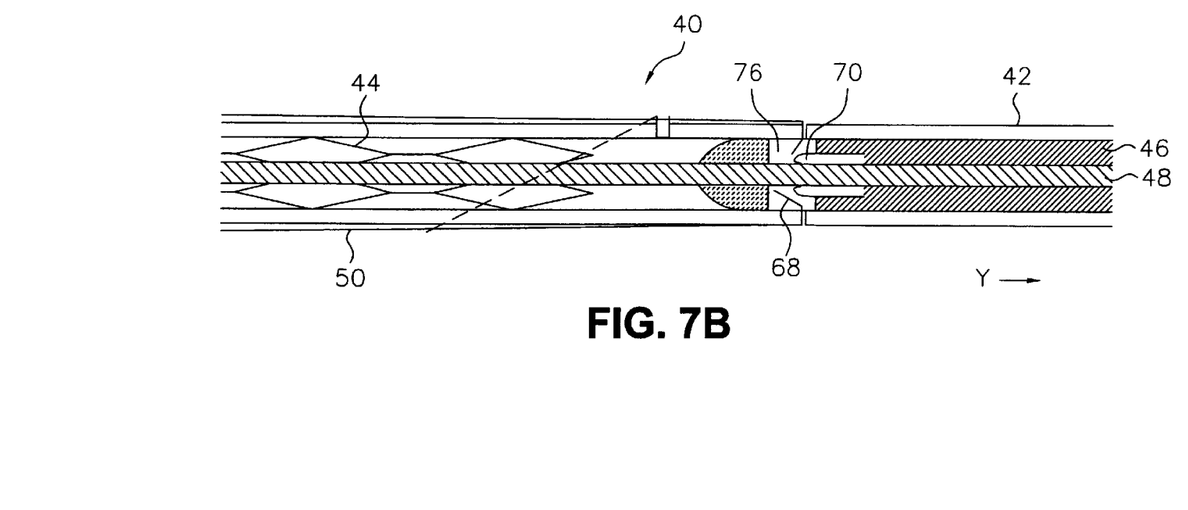
Figure 7C:
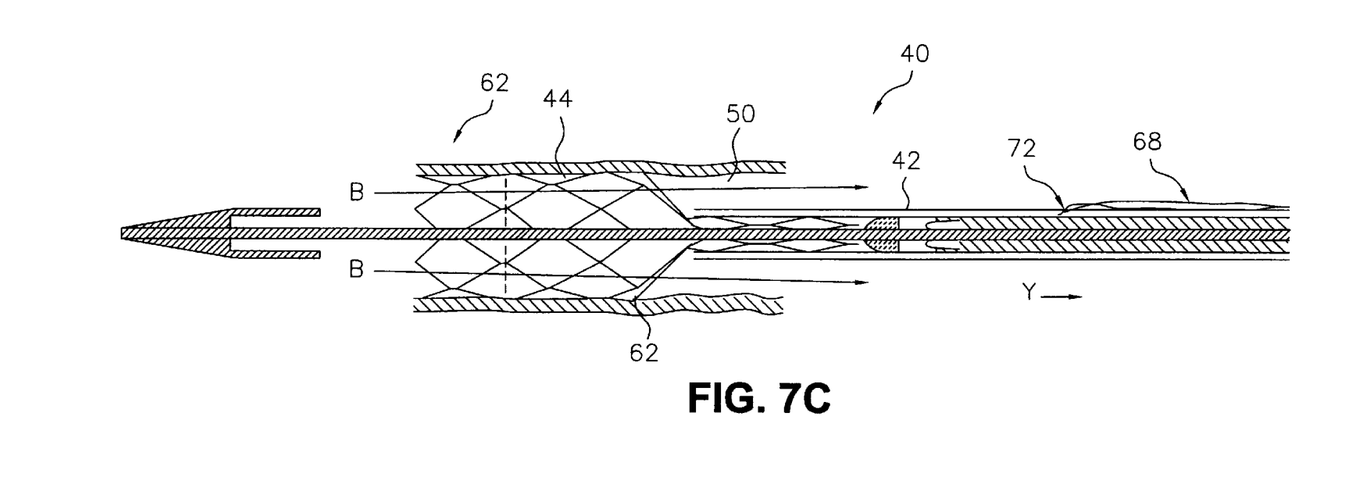
Figure 7D:
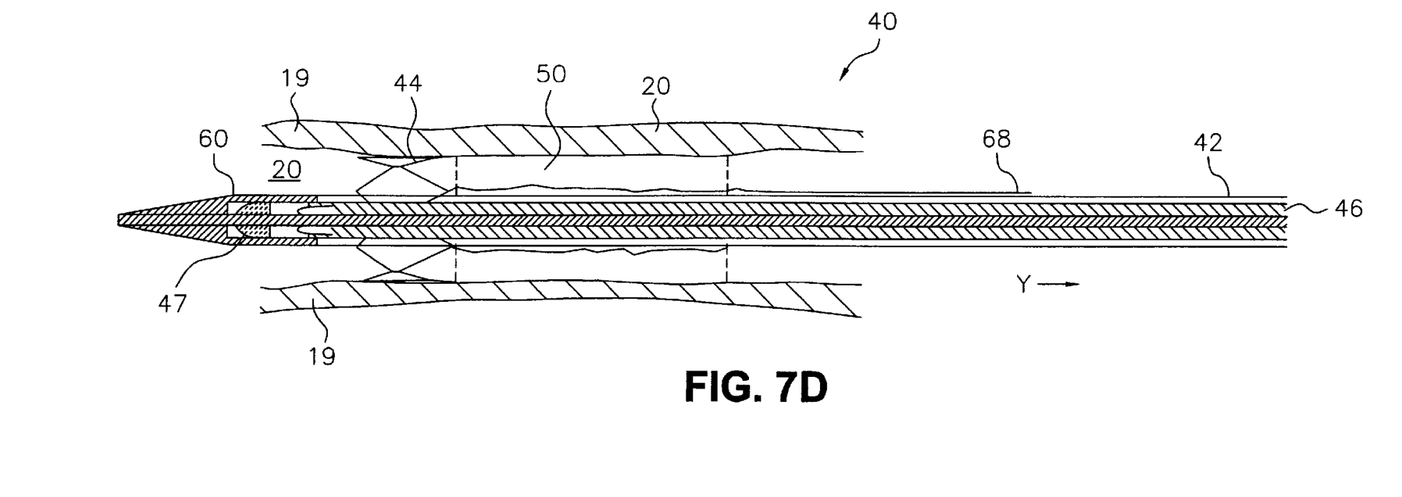
FIG. 7D is a partial longitudinal section schematic illustration of the deployed stent and the stent delivery system prepared for withdrawal after the deployment step shown in FIG. 7C.

Introducer 40 is used to carry out a method for endoluminally deploying a stent and overlying graft without blocking endoluminal fluid flow during deployment, as shown in FIGS. 7A–D. First, stent 44 and overlying graft 50 are compressed and loaded into stent delivery system 40 having the components previously described herein and assembled as shown in FIG. 3A. Next, the stent delivery system is navigated to a desired deployment location over a guidewire (not shown) or by other means known in the art. Then, at the deployment location, stent distal end 62 is released by moving inner core 48 distally relative to stent sheath 42 along arrow Z, as shown in FIG. 7A. Then, stent sheath 42 is retracted proximally relative to stent 44 along arrow Y, thus pulling suture 68 in window 76 across cutter 70 of pusher 46 and severing the suture as shown in FIG. 7B. With suture 68 cut, graft 50 expands so that blood or other endoluminal fluid flows along arrows B through stent 44 and between stent sheath 42 and the graft, as is shown in FIG. 7C. Suture 68 is retained on stent sheath 42 in two pieces, each piece tied at one end through tie-holes 72 in the stent sheath and carried by the motion of the stent sheath and the endoluminal fluid flow in the direction of arrow B. Stent sheath 42 is retracted along arrow Y until stent 44 is completely deployed in a configuration biasing graft 50 against the walls 19 of the body lumen 20, as shown in FIG. 7D.

Stent delivery system 40 may then be prepared for withdrawal from the body by advancing pusher 46 inside tip sheath 60 and advancing stent sheath 42 until it is adjacent to the tip sheath as also shown in FIG. 7D. Rounded distal end 47 of pusher 46 is advantageous for guiding the pusher into tip sheath 60, which is especially useful when stent delivery system 40 is used in an area of curved anatomy. With the stent delivery system 40 in a closed configuration as shown in FIG. 7D, tip sheath 60 is less likely to snag on stent 44 or on walls 19 of lumen 20 during withdrawal, than if left in an open configuration with a gap between stent sheath 42 and the tip sheath, such as is shown in FIG. 7C.

Figure 8:
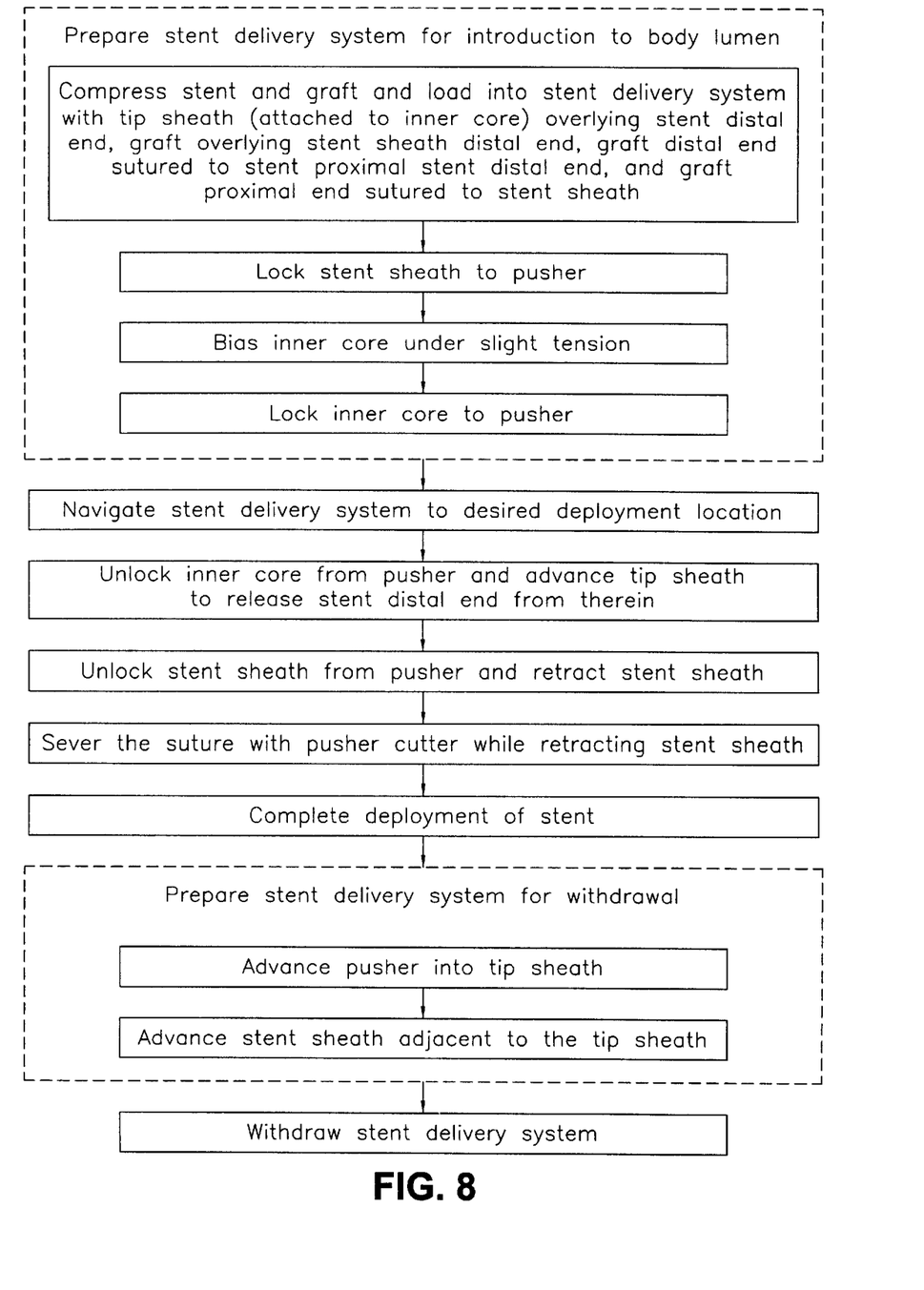
FIG. 8 is a flowchart depicting exemplary method steps for deployment of a stent and graft according to the present invention.

Prior to deployment, stent sheath 42 may be locked to pusher 46 and inner core 48 may also be locked to the pusher. The locking of these components together is typically accomplished at the handles located at the proximal end of the delivery system (not shown) and that remain outside the body during the deployment procedure. Inner core 48 may also be biased under slight tension prior to locking and introduction of stent delivery system 40 into the body lumen so that tip sheath 60 does not become displaced relative to stent sheath 42 in curved anatomy. Thus, when stent delivery system 40 is introduced into the body in a locked configuration, the step of advancing inner core 48 relative to stent sheath 42 first comprises unlocking the inner core from pusher 46 prior to moving the inner core. Similarly, the step of retracting stent sheath 42 further comprises unlocking the stent sheath from pusher 46 prior to moving the sheath. Thus, one exemplary method for deployment of a stent and graft according to the present invention may include all the steps as depicted in the self-explanatory flowchart of FIG. 8.

Figure 9:
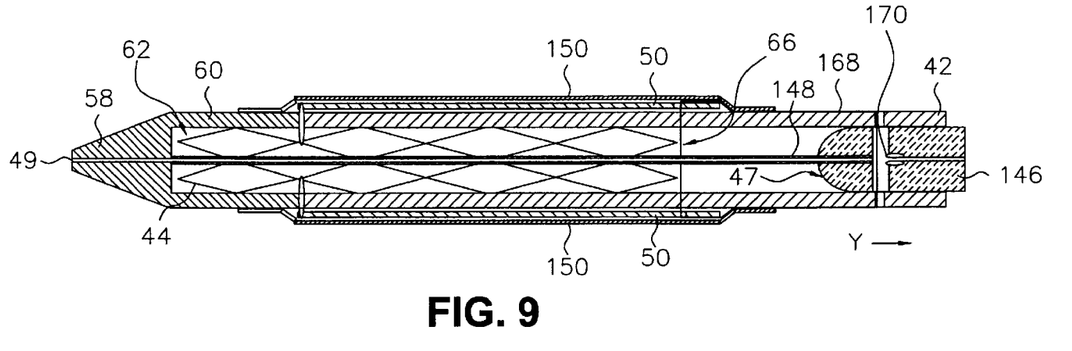
FIG. 9 is a longitudinal section schematic illustration of an alternate embodiment of an assembled exemplary stent delivery system of the present invention.

Inner core 48 attached to tip 58 (and attached to tip sheath 60, where present) may be mounted axially through inner lumen 56 of pusher 46 as shown in FIGS. 3A–C and 7A–D, or, referring now to FIG. 9, inner core 148 may instead be mounted to distal end of pusher 146. In such a configuration when tip sheath 60 is also present, sheath 42 is retracted in a single motion in the direction of arrow Y to simultaneously pull distal end 62 of stent 44 from out of tip sheath 60, allowing it to expand, while also severing suture 168 against cutter 170 within pusher 146. As retraction of sheath 42 continues in the direction of arrow Y after stent distal end 62 is expanded, the proximal end 66 of stent 44 contacts distal end 47 of pusher 146, which then pushes the stent out from within stent sheath 42.

Also illustrated in FIG. 9 is a temporary protective wrapper 150 over graft 50. The wrapper may be adapted to be split or otherwise peeled or torn away prior to inserting the delivery system within the body lumen. Such a temporary wrapper protects the graft and keeps it compressed against the sheath until just prior to deployment. Such a wrapper may be heat-set in place during a heat setting step that also may heat-set the graft into a low profile. This wrapper may be particularly useful in an embodiment of this invention wherein the proximal end of the graft is not attached to the sheath at all (not shown), but instead remains in its heat-set position wrapped about stent sheath 42 until stent 44 starts to expand. The heat-set configuration is undone as stent 44 expands and blood flows between graft 50 and stent sheath 42.

Further illustrated in FIG. 9 is an embodiment wherein suture 168 is secured to graft 50 rather than being secured through tie-holes in stent sheath 42. In this configuration, when suture 168 is broken, it remains connected to graft 50 rather than to sheath 42. Suture 168 preferably comprises a resorbable suture material to reduce risk of embolism from the trailing suture segments.

Figure 10A:
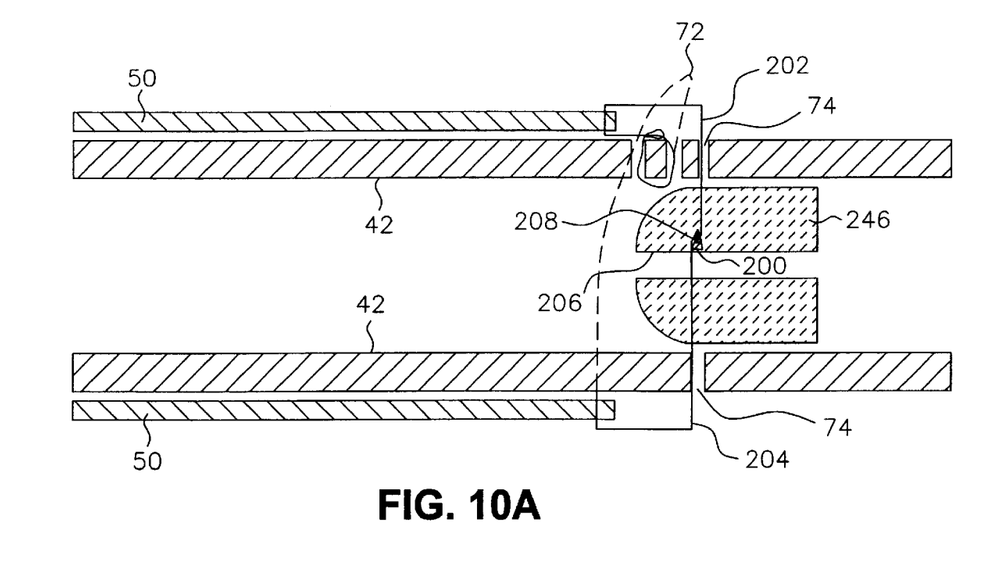
FIGS. 10A and 10B are a longitudinal section schematic illustration of an exemplary introducer embodiment wherein the graft is secured via a slip knot, and a detailed illustration of the knot, respectively.
Figure 10B:
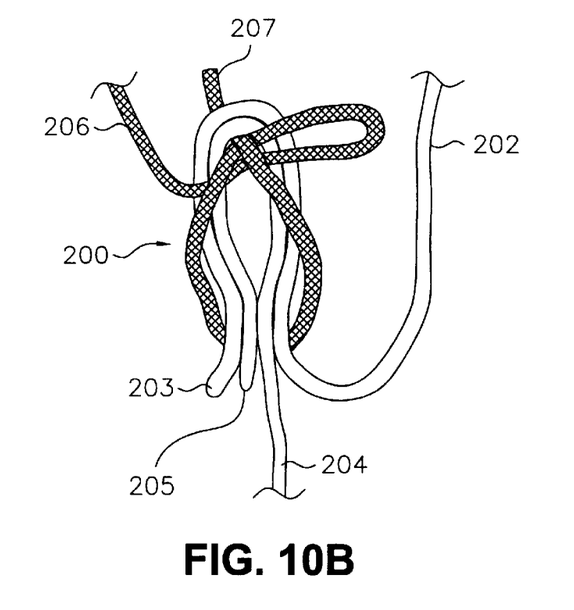

In yet another embodiment, the suture used for attaching the graft to the sheath may be a slip knot 200, such as shown in FIGS. 10A and 10B, that may be untied to release the suture. Exemplary slip knot 200, as shown in more detail in FIG. 10B, may comprise a first suture 202 and a second suture 204 that each hold down graft 50 and are secured to stent sheath 42 at a connection point, such as at tie holes 72, and a third suture 206 that has a slipped end 208. Slipped end may be attached to pusher 246 (as shown in FIG. 10A) or to the inner core (not shown) so that relative movement of the stent sheath relative to the pusher or inner core unties the knot, or the slipped end may be trailed as a drawstring outside the body lumen. First suture 202, second suture 204, and third suture 206 each also have free ends 203, 205, and 207, respectively, that are tied together in slip knot 200. Knot 200 as illustrated in FIG. 10B is a modified sheet bend, shown prior to tightening, for clarity. Other slip knot configurations known in the art may also be chosen, based on suture properties and manufacturing considerations.

To provide a slip knot embodiment such as shown in FIG. 10A, slip knot 200 may be first created at free end 203 of first suture 202, free end 205 of second 204, and free end 207 of third suture 206 having slipped end 208 attached to pusher 246. Then the ends of sutures 202 and 204 opposite free ends 203 and 205, respectively, are threaded inside sheath 42 and out through through-holes 74, and pusher 246 is threaded inside sheath 42 into its position for deployment into the body lumen. Sutures 202 and 204 may then be secured to graft 50 and tie-holes 72 as shown in FIG. 10A.

Attachment means other than sutures may also be used for securing the proximal end of the graft to the sheath, or as mentioned above, the sheath may be left unattached at the proximal end, constrained about the sheath only by the effects of a heat-set step. Alternatively, the fluid dynamics of opposing blood flow may be sufficient to retain the proximal end circumference of the graft and preclude flow obstruction by the graft both prior to and during deployment.

Figure 11:
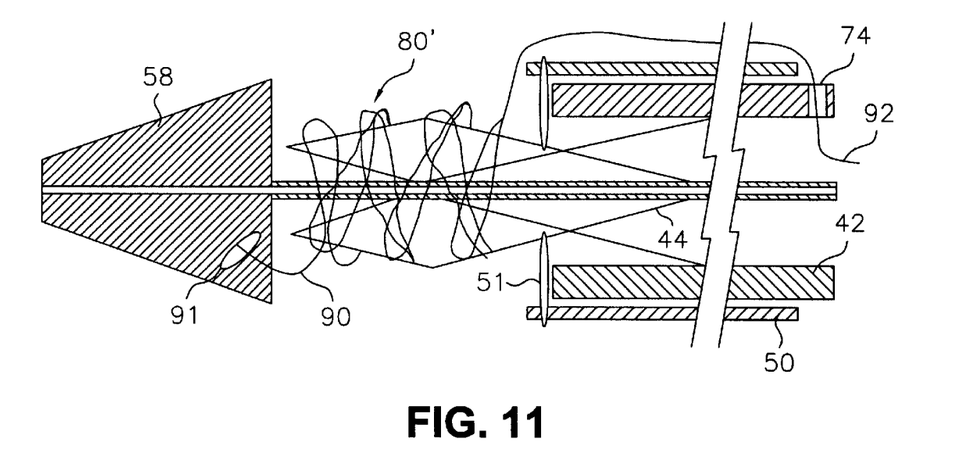
FIG. 11 is a partial longitudinal section schematic illustration of a distal portion of an exemplary stent delivery system having a crochet weave securing the distal end of the stent.

Distal end 62 of stent 44 may extend distally of distal end 64 of graft 50 as shown in the embodiment illustrated in FIGS. 3A–C and 7A–D, or the graft distal end may be attached directly to the stent distal end. Where the stent and graft distal ends are attached, tip sheath 60 is unnecessary, but tip 58 may still be present. Where stent distal end 62 does extend distally of graft distal end 64, the stent distal end may be secured to core 48 by means other than tip sheath 60, as shown in FIG. 3B. For instance, as shown in FIG. 11, crochet weave 80', having a distal end 90 pinched within slot 91 in catheter tip 58 and a proximal end 92 threaded into through-hole 74 in stent sheath 42 and trailed proximally outside the body lumen to be pulled like a drawstring, can be used in accordance with the general crochet weave configuration described herein earlier with respect to FIG. 4B.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A method for endoluminally deploying a stent and overlying biocompatible graft cover in a distal deployment location inside a lumen from a proximal access location, said lumen defining an interior space therein, the method comprising the steps of:
   a) compressing the stent and graft and loading the compressed stent and compressed graft into a delivery system, the delivery system comprising a stent sheath having a distal end located upstream relative to a flow direction of intraluminal fluid in the lumen, the compressed stent underlying the stent sheath and having a distal end, and the compressed graft overlying the stent sheath along the length of the stent and releasably retained in a compressed state surrounding said sheath, said graft having a distal end attached to the stent at or proximal the stent distal end and an outer surface exposed to the interior space of said lumen during deployment;
   b) inserting the delivery system into a lumen and navigating said delivery system through said lumen so that said stent is at a desired deployment location;
   c) proximally displacing the stent sheath relative to the distal end of the stent, allowing the stent distal end to expand, and allowing endoluminal fluid to flow between the stent sheath and the graft so that the graft becomes radially distanced from the stent sheath; and
   d) completing deployment of the stent so that it biases the graft against the body lumen.

2. The method of claim 1 wherein the delivery system further comprises a temporary, protective wrapper over said biocompatible graft cover and in which the method further comprises prior to step (b) removing said temporary, protective wrapper.

3. The method of claim 1 wherein the stent distal end is spaced distally from the stent sheath distal end stent and the delivery system further comprises a tip comprising a tip sheath overlying the stent distal end and attached to an inner core extending axially through the stent, and wherein step (c) comprises first releasing the stent distal end from the tip sheath by displacing the inner core distally relative to the stent sheath, and then retracting said stent sheath to deploy said stent.

4. The method of claim 3 wherein the delivery system further comprises a pusher underlying the stent sheath proximal to the stent, said pusher having a distal end attached to said inner core, wherein moving the inner core distally relative to the stent sheath to release the stent distal end from the tip sheath in step (c) comprises a single, continuous, proximal retraction of the stent sheath that also displaces said pusher distally relative to said stent sheath to deploy said stent.

5. The method of claim 4 wherein step (a) further comprises locking said stent sheath to said pusher, biasing said inner core under slight tension, and locking said inner core to said pusher; and wherein step (c) further comprises unlocking said inner core from said pusher prior to distally moving the inner core, and unlocking said stent sheath from said pusher prior to retracting said stent sheath.

6. The method of claim 3 wherein the delivery system further comprises a pusher underlying the stent sheath proximal to the stent, said pusher having an inner lumen axially therethrough within which the inner core is axially mounted, wherein step (c) comprises first advancing the inner core distally relative to the stent sheath and pusher to release the stent distal end from the tip sheath, and then retracting said stent sheath to deploy said stent.

7. The method of claim 1 wherein the biocompatible graft further comprises a proximal end attached to the stent sheath by a releasable attachment, and wherein the method further comprises in step (c) releasing the releasable attachment prior to the endoluminal fluid flowing between the stent sheath and the graft.

8. The method of claim 7 wherein the releasable attachment is a crochet weave wrapped around said graft and comprising a continuous filament having a proximal end trailing outside said lumen, and in which step (c) further comprises pulling said proximal end and untying said crochet weave.

9. The method of claim 7 wherein the releasable attachment is a bead of adhesive between said graft and said stent sheath and in which step (c) further comprises releasing said attachment by softening or dissolving said adhesive sufficiently via exposure to said intraluminal fluid to allow said graft to be pulled away from said stent sheath.

10. The method of claim 7 wherein the stent sheath comprises a slot therein adapted to receive a portion of the graft and the pusher comprises an indented portion thereof, the releasable attachment comprising a portion of the graft disposed within the slot and pinched between the pusher and the stent sheath prior to and during introduction into the lumen, and in which step (c) further comprises releasing the attachment by moving the stent sheath relative to the pusher until the indented portion of the pusher aligns with the slot in the stent sheath and the portion of the graft disposed within the slot is no longer pinched between the pusher and the stent sheath.

11. The method of claim 7 wherein the releasable attachment is a suture and in which step (c) further comprises releasing said suture by cutting the suture or untying a slip-knot in said suture.

12. The method of claim 11 wherein the delivery system further comprises a pusher underlying the stent sheath proximal to the stent, the pusher comprising an inner lumen axially therethrough and a cutter, a tip comprising a tip sheath overlying a distal end of the stent and attached to an inner core extending axially through the stent and through the pusher inner lumen, wherein step (c) comprises first moving the inner core distally relative to the stent sheath to release the stent distal end from the tip sheath and then moving said pusher relative to said stent sheath to cut said suture.

13. The method of claim 12 wherein the stent sheath has a circumference having therein a suture connection point and a set of radially opposite through-holes and the pusher has a distal end having therein a window distally adjacent the cutter, the method further comprising in step (a) radially aligning the pusher window with the stent sheath through-holes, and suturing the graft to the stent sheath by anchoring opposite ends of the suture through the suture connection point and threading an intermediate portion of the suture through the graft, the stent sheath through-holes, and the pusher window.

14. The method of claim 13 further comprising suturing the graft to the stent sheath by the steps of:
   i) anchoring a first end of the suture at the suture connection point,
   ii) extending the suture along the stent sheath;
   iii) piercing the graft one or more times with the suture;
   iv) extending the suture along the stent sheath;
   v) entering the stent sheath radially through one of the through-holes, extending the suture through the pusher window, and exiting the stent sheath through the opposite through-hole;
   vi) extending the suture along the stent sheath;
   vii) piercing the graft one or more times with the suture;
   viii) extending the suture semi-circumferentially around the sheath; and
   ix) anchoring a second end of the suture at the suture connection point or to the first end of the suture.

15. The method of claim 14 wherein the steps are carried out in sequential order from (i) to (ix), and steps (ii) and (vi) comprise extending the suture distally and step (iv) comprises extending the suture proximally.

16. The method of claim 14 wherein the steps are carried out in reverse sequential order from (ix) to (i), and steps (ii) and (vi) comprise extending the suture proximally and step (iv) comprises extending the suture distally.

17. The method of claim 1 further comprising the steps of:
   e) preparing the delivery system for withdrawal, and
   f) withdrawing the delivery system.

18. The method of claim 1 further comprising the steps of:
   e) preparing the delivery system for withdrawal by
      i) advancing the pusher into the tip sheath; and
      ii) advancing the stent sheath until a distal end of the stent sheath is adjacent to a proximal end of the tip sheath, and
   f) withdrawing the delivery system.

* * * * *